United States Patent [19]

Petri et al.

[11] Patent Number: 5,260,429
[45] Date of Patent: Nov. 9, 1993

[54] PURIFIED DNA OF THE 170-KD SURFACE GAL/GALNAC ADHERENCE LECTIN OF PATHOGENIC E. HISTOLYTICA

[75] Inventors: William Petri, Glen Allen; Barbara Mann, Charlottesville, both of Va.

[73] Assignee: The University of Virginia Alumni Patents Foundation, Charlottesville, Va.

[21] Appl. No.: 615,719

[22] Filed: Nov. 21, 1990

Related U.S. Application Data

[63] Continuation-in-part of Ser. No. 479,691, Feb. 13, 1990, which is a continuation-in-part of Ser. No. 456,579, Dec. 29, 1989, Pat. No. 5,004,608, which is a continuation of Ser. No. 143,626, Jan. 13, 1988, abandoned.

[51] Int. Cl.$^5$ ................ C07H 17/00; C07H 23/00
[52] U.S. Cl. .................. 536/23.4; 536/23.5; 536/23.1; 536/25.4
[58] Field of Search ............ 435/6, 29, 91; 436/501, 436/504; 935/19, 20, 22, 27, 31

[56] References Cited

U.S. PATENT DOCUMENTS 4,683,195  7/1987  Mullis et al. ................ 435/6

OTHER PUBLICATIONS

Tannich et al. P.N.A.S. 88:1849 (1991).
Sammelson et al. J. Clin. Microb. 27(4):671 (1989).
Mann et al. P.N.A.S. 88:3248 (1991).
Mirelman et al., *Infection & Immunity* (1986) 54(3):827–832.
Petri et al., *J. Biol. Chem.* (1989) 264(5):3007–3012.
Ravdin et al., *Infection & Immunity* (1986) 53(1):1–5.
Petri et al., *J. Clin. Invest.* (1987) 80:1238–1244.
Petri, Jr. et al., *Am. J. Med. Sci.* (1989) 296(7):163–165.
Root et al., *Arch. Invest. Med.* (Mex) (1978) 9:Supplement 1:203–210.
Palacios et al., *Arch. Invest. Med.* (Mex) (1978) 9:Supplement 1:339–348.
Randall et al., *Trans. Roy. Soc. Trop. Med. Hyg.* (1984) 78:593–595.
Grundy, *Trans. Roy. Soc. Trop. Med. Hyg.* (1982) 76(3):396–400.
Ungar, *Am J. Trop. Med. Hyg.* (1985) 34(3):465–472.
Ravdin ed., *Amebiasis: Human Infection by Entamoeba Histolytica*, (1988) Wiley Medical Publishing Co., pp. 661–663.
Ravdin ed., *Amebiasis: Human Infection by Entamoeba Histolytica*, (1988) Wiley Medical Publishing Co., pp. 646–649.
Garfinkel et al., *Infection & Immunity* (1989) 57:(3):926–931.
Tannich et al., *Proc. Natl. Acad. Sci.* (1989) 86:5118–5122.
Strachan et al., *Lancet* (Mar. 12, 1988) pp. 561–562.

*Primary Examiner*—Robert A. Wax
*Assistant Examiner*—Miguel Escallon
*Attorney, Agent, or Firm*—Morrison & Foerster

[57] ABSTRACT cDNA encoding the 170 kd subunit of Gal/GalNAc lectin in various strains of *E. histolytica* is provided. Availability of this cDNA permits the use of diagnostic assays to distinguish pathogenic from nonpathogenic strains based on DNA hybridization, and further permits antisense approaches to interrupting the production of this lectin.

1 Claim, 9 Drawing Sheets

```
          10              20              30              40
TGC ATT GAG ACT TGT TTC GAC TTG GAC CAC ATT ATC ATG AAT TTA CAG
 C   I   E   T   C   F   D   L   D   H   I   I   M   N   L   Q 50              60              70              80              90
GTA ATG ATG AAG TTA ATG CAA CAA TCA CTG CAC TTT TCA AAG GAA TTA
 V   M   M   K   L   M   Q   Q   S   L   H   F   S   K   E   L 100             110             120             130             140
GAG CCT AAT TTA ACA GAA AGA TGT GAT AGA GAT AAA TGT TCA GGA TTT
 E   P   N   L   T   E   R   C   D   R   D   K   C   S   G   F 150             160             170             180             190
TGT GAT GCA ATG AAT AGA TGC ACA TGT CCA ATG TGT TGT GAG AAT GAT
 C   D   A   M   N   R   C   T   C   P   M   C   C   E   N   D 200             210             220             230             240
TGT TTC TAT ACA TCC TGT GAT GTA GAA ACA GGA TCA TGT ATT CCA TGG
 C   F   Y   T   S   C   D   V   E   T   G   S   C   I   P   W 250             260             270             280
CCT AAA GCT AAA CCA AAA GCA AAG AAA GAA TGT CCA GCA ACA TGT GTA
 P   K   A   K   P   K   A   K   K   E   C   P   A   T   C   V 290             300             310             320             330
GGC TCA TAT GAA TGT AAA GAT CTT GAA GGA TGT GTT GTT ACA AAA TAT
 G   S   Y   E   C   K   D   L   E   G   C   V   V   T   K   Y 340             350             360             370             380
AAT GAC ACA TGC CAA CCA AAA GTG AAA TGC ATG GTA CCA TAT TGT GAT
 N   D   T   C   Q   P   K   V   K   C   M   V   P   Y   C   D 390             400             410             420             430
    AAT GAT AAG AAT CTA ACT GAA GTA TGT AAA CAA AAA GCT AAT TGT GAA
     N   D   K   N   L   T   E   V   C   K   Q   K   A   N   C   E
```

```
         10              20              30              40
TGC ATT GAG ACT TGT TTC GAC TTG GAC CAC ATT ATC ATG AAT TTA CAG
 C   I   E   T   C   F   D   L   D   H   I   I   M   N   L   Q 50              60              70              80              90
GTA ATG ATG AAG TTA ATG CAA CAA TCA CTG CAC TTT TCA AAG GAA TTA
 V   M   M   K   L   M   Q   Q   S   L   H   F   S   K   E   L 100             110             120             130             140
GAG CCT AAT TTA ACA GAA AGA TGT GAT AGA GAT AAA TGT TCA GGA TTT
 E   P   N   L   T   E   R   C   D   R   D   K   C   S   G   F 150             160             170             180             190
TGT GAT GCA ATG AAT AGA TGC ACA TGT CCA ATG TGT TGT GAG AAT GAT
 C   D   A   M   N   R   C   T   C   P   M   C   C   E   N   D 200             210             220             230             240
TGT TTC TAT ACA TCC TGT GAT GTA GAA ACA GGA TCA TGT ATT CCA TGG
 C   F   Y   T   S   C   D   V   E   T   G   S   C   I   P   W 250             260             270             280
CCT AAA GCT AAA CCA AAA GCA AAG AAA GAA TGT CCA GCA ACA TGT GTA
 P   K   A   K   P   K   A   K   K   E   C   P   A   T   C   V 290             300             310             320             330
GGC TCA TAT GAA TGT AAA GAT CTT GAA GGA TGT GTT GTT ACA AAA TAT
 G   S   Y   E   C   K   D   L   E   G   C   V   V   T   K   Y 340             350             360             370             380
AAT GAC ACA TGC CAA CCA AAA GTG AAA TGC ATG GTA CCA TAT TGT GAT
 N   D   T   C   Q   P   K   V   K   C   M   V   P   Y   C   D 390             400             410             420             430
AAT GAT AAG AAT CTA ACT GAA GTA TGT AAA CAA AAA GCT AAT TGT GAA
 N   D   K   N   L   T   E   V   C   K   Q   K   A   N   C   E
```

FIG. 1A

```
       440              450              460              470              480
GCA GAT CAA AAA CCA AGT TCT GAT GGA TAT TGT TGG AGT TAT ACA TGT
 A   D   Q   K   P   S   S   D   G   Y   C   W   S   Y   T   C 490              500              510              520
GAC CAA ACT ACT GGT TTT TGT AAG AAA GAT AAA CGA GGT AAA GAA ATG
 D   Q   T   T   G   F   C   K   K   D   K   R   G   K   E   M 530              540              550              560              570
TGT ACA GGA AAG ACA AAT AAT TGT CAA GAA TAT GTT TGT GAT TCA GAA
 C   T   G   K   T   N   N   C   Q   E   Y   V   C   D   S   E 580              590              600              610         620
CAA AGA TGT AGT GTT AGA GAT AAA GTA TGT GTA AAA ACA TCA CCA TAC
 Q   R   C   S   V   R   D   K   V   C   V   K   T   S   P   Y 630              640              650              660           670
ATT GAA ATG TCA TGT TAT GTA GCC AAG TGT AAT CTC AAT ACA GGT ATG
 I   E   M   S   C   Y   V   A   K   C   N   L   N   T   G   M 680              690              700              710          720
TGT GAG AAC AGA TTA TCA TGT GAT ACA TAC TCA TCA TGT GGT GGA GAT
 C   E   N   R   L   S   C   D   T   Y   S   S   C   G   G   D 730              740              750              760
TCT ACA GGA TCA GTA TGT AAA TGT GAT TCT ACA ACT GGT AAT AAA TGT
 S   T   G   S   V   C   K   C   D   S   T   T   G   N   K   C 770              780              790              800              810
CAA TGT AAT AAA GTA AAA AAT GGT AAT TAT TGT AAT TCT AAA AAC CAT
 Q   C   N   K   V   K   N   G   N   Y   C   N   S   K   N   H 820              830              840              850              860
GAA ATT TGT GAT TAT ACA GGA ACA ACA CCA CAA TGT AAA GTG TCT AAT
 E   I   C   D   Y   T   G   T   T   P   Q   C   K   V   S   N
```

FIG. 1B

```
      870              880              890              900              910
TGT ACA GAA GAT CTT GTT AGA GAT GGA TGT CTT ATT AAG AGA TGC AAT
 C   T   E   D   L   V   R   D   G   C   L   I   K   R   C   N 920              930              940              950              960
GAA ACA AGT AAA ACA ACA TAT TGG GAG AAT GTT GAT TGT TCA AAC ACT
 E   T   S   K   T   T   Y   W   E   N   V   D   C   S   N   T 970              980              990             1000
AAG ATT GAA TTT GCT AAA GAT GAT AAA TCT GAA ACT ATG TGT AAA CAA
 K   I   E   F   A   K   D   D   K   S   E   T   M   C   K   Q 1010            1020             1030             1040             1050
TAT TAT TCA ACT ACA TGT TTG AAT GGA AAA TGT GTT GTT CAA GCA GTT
 Y   Y   S   T   T   C   L   N   G   K   C   V   V   Q   A   V 1060             1070             1080             1090             1100
GGT GAT GTT TCT AAT GTA GGA TGT GGA TAT TGT TCA ATG GGA ACA GAT
 G   D   V   S   N   V   G   C   G   Y   C   S   M   G   T   D 1110             1120             1130             1140             1150
AAT ATT ATT ACA TAT CAT GAT GAT TGT AAT TCA CGT AAA TCA CAA TGT
 N   I   I   T   Y   H   D   D   C   N   S   R   K   S   Q   C 1160             1170             1180             1190             1200
GGA AAC TTT AAT GGT AAA TGT ATT AAA GGC AGT GAC AAT TCT TAT TCT
 G   N   F   N   G   K   C   I   K   G   S   D   N   S   Y   S 1210             1220             1230             1240
TGT GTA TTT GAA AAA GAT AAA ACT TCT TCT AAA TCA GAT AAT GAT ATT
 C   V   F   E   K   D   K   T   S   S   K   S   D   N   D   I 1250             1260             1270             1280             1290
TGT GCT GAA TGT TCT AGT TTA ACA TGT CCA GCT GAT ACT ACA TAC AGA
 C   A   E   C   S   S   L   T   C   P   A   D   T   T   Y   R
```

FIG. 1C

```
      1300          1310         1320         1330          1340
 ACA TAT ACA TAT GAC TCA AAA ACA GGA ACA TGT AAA GCA ACT GTT CAA
  T   Y   T   Y   D   S   K   T   G   T   C   K   A   T   V   Q 1350         1360         1370         1380          1390
 CCA ACA CCA GCA TGT TCA GTA TGT GAA AGT GGT AAA TTT GTA GAG AAA
  P   T   P   A   C   S   V   C   E   S   G   K   F   V   E   K 1400         1410         1420         1430         1440
 TGC AAA GAT CAA AAA TTA GAA CGT AAA GTC ACT TTA GAA AAT GGA AAA
  C   K   D   Q   K   L   E   R   K   V   T   L   E   N   G   K 1450         1460         1470         1480
 GAA TAT AAA TAC ACC ATT CCA AAA GAT TGT GTC AAT GAA CAA TGC ATT
  E   Y   K   Y   T   I   P   K   D   C   V   N   E   Q   C   I 1490         1500         1510         1520         1530
 CCA AGA ACA TAC ATA GAT TGT TTA GGT AAT GAT GAT AAC TTT AAA TCT
  P   R   T   Y   I   D   C   L   G   N   D   D   N   F   K   S 1540         1550         1560         1570          1580
 ATT TAT AAC TTC TAT TTA CCA TGT CAA GCA TAT GTT ACA GCT ACC TAT
  I   Y   N   F   Y   L   P   C   Q   A   Y   V   T   A   T   Y 1590         1600         1610         1620         1630
 CAT TAC AGT TCA TTA TTC AAT TTA ACT AGT TAT AAA CTT CAC TTA CCA
  H   Y   S   S   L   F   N   L   T   S   Y   K   L   H   L   P 1640         1650         1660         1670         1680
 CAA AGT GAA GAA TTT ATG AAA GAG GCA GAC AAA GAA GCA TAT TGT ACA
  Q   S   E   E   F   M   K   E   A   D   K   E   A   Y   C   T 1690         1700         1710         1720
 TAC GAA ATA ACA ACA AGA GAA TGT AAA ACA TGT TCA TTA ATT GAA ACT
  Y   E   I   T   T   R   E   C   K   T   C   S   L   I   E   T
```

FIG. 1D

```
         1740              1750              1760              1770
 GA GAA AAA GTC CAA GAA GTT GAT TTG TGT GCA GAA GAA ACT AAG AAT
 R  E   K   V   Q   E   V   D   L   C   A   E   E   T   K   N 1780          1790          1800          1810          1820
 GA GGA GTT CCA TTC AAA TGT AAG AAT AAC AAT TGC ATT ATT GAT CCT
 G  G   V   P   F   K   C   K   N   N   N   C   I   I   D   P 1830          1840          1850          1860          1870
 AAC TTT GAT TGT CAA CCT ATT GAA TGT AAG ATT CAA GAG ATT GTT ATT
 N   F   D   C   Q   P   I   E   C   K   I   Q   E   I   V   I 1880          1890          1900          1910          1920
 ACA GAA AAA GAT GGA ATA AAA ACA ACA ACA TGT AAA AAT ACT ACA AAA
 T   E   K   D   G   I   K   T   T   T   C   K   N   T   T   K 1930          1940          1950          1960
 GCA ACA TGT GAC ACT AAC AAT AAG AGA ATA GAA GAT GCA CGT AAA GCA
 A   T   C   D   T   N   N   K   R   I   E   D   A   R   K   A 1970          1980          1990          2000          2010
 TTC ATT GAA GGA AAA GAA GGA ATT GAG CAA GTA GAA TGT GCA AGT ACT
 F   I   E   G   K   E   G   I   E   Q   V   E   C   A   S   T 2020          2030          2040          2050          2060
 GTT TGT CAA AAT GAT AAT AGT TGT CCA ATT ATT ACT GAT GTA GAA AAA
 V   C   Q   N   D   N   S   C   P   I   I   T   D   V   E   K 2070          2080          2090          2100          2110
 TGT AAT CAA AAC ACA GAA GTA GAT TAT GGA TGT AAA GCA ATG ACA GGA
 C   N   Q   N   T   E   V   D   Y   G   C   K   A   M   T   G 2120          2130          2140          2150          2160
 GAA TGT GAT GGT ACT ACA TAT CTT TGT AAA TTT GTA CAA CTT ACT GAT
 E   C   D   G   T   T   Y   L   C   K   F   V   Q   L   T   D
```

FIG. 1E

```
              2170          2180          2190          2200
         GAT CCA TCA TTA GAT AGT GAA CAT TTT AGA ACT AAA TCA GGA GTT GAA
          D   P   S   L   D   S   E   H   F   R   T   K   S   G   V   E 2210          2220          2230          2240          2250
      CTT AAC AAT GCA TGT TTG AAA TAT AAA TGT GTT GAG AGT AAA GGA AGT
       L   N   N   A   C   L   K   Y   K   C   V   E   S   K   G   S 2260          2270          2280          2290          2300
      GAT GGA AAA ATC ACA CAT AAA TGG GAA ATT GAT ACA GAA CGA TCA AAT
       D   G   K   I   T   H   K   W   E   I   D   T   E   R   S   N 2310          2320          2330          2340          2350
      GCT AAT CCA AAA CCA AGA AAT CCA TGC GAA ACC GCA ACA TGT AAT CAA
       A   N   P   K   P   R   N   P   C   E   T   A   T   C   N   Q 2360          2370          2380          2390          2400
      ACA ACT GGA GAA ACT ATT TAC ACA AAG AAA ACA TGT ACT GTT TCA GAA
       T   T   G   E   T   I   Y   T   K   K   T   C   T   V   S   E 2410          2420          2430          2440
         TTC CCA ACA ATC ACA CCA AAT CAA GGA AGA TGT TTC TAT TGT CAA TGT
          F   P   T   I   T   P   N   Q   G   R   C   F   Y   C   Q   C 2450          2460          2470          2480          2490
      TCA TAT CTT GAC GGT TCA TCA GTT CTT ACT ATG TAT GGA GAA ACA GAT
       S   Y   L   D   G   S   S   V   L   T   M   Y   G   E   T   D 2500          2510          2520          2530          2540
      AAA GAA TAT TAT GAT CTT GAT GCA TGT GGT AAT TGT CGT GTT TGG AAT
       K   E   Y   Y   D   L   D   A   C   G   N   C   R   V   W   N 2550          2560          2570          2580          2590
      CAG ACA GAT AGA ACA CAA CAA CTT AAT AAT CAC ACC GAG TGT ATT CTC
       Q   T   D   R   T   Q   Q   L   N   N   H   T   E   C   I   L
```

FIG. 1F

```
      2600            2610            2620            2630            2640
GCA GGA GAA ATT AAT AAT GTT GGA GCT ATT GCA GCG GCA ACT ACT GTG
 A   G   E   I   N   N   V   G   A   I   A   A   A   T   T   V 2650            2660            2670            2680
GCT GCT GTT ATA GTT GCA GTT GTA GTT GCA TTA ATT GTT GTT TCT ATT
 A   A   V   I   V   A   V   V   V   A   L   I   V   V   S   I 2690            2700            2710            2720            2730
GGA TTA TTT AAG ACT TAT CAA CTT GTT TCA TCA GCT ATG AAG AAT GCC
 G   L   F   K   T   Y   Q   L   V   S   S   A   M   K   N   A 2740            2750            2760            2770            2780
ATT ACA ATA ACT AAT GAA AAT GCA GAA TAT GTT GGA GCA GAT AAT GAA
 I   T   I   T   N   E   N   A   E   Y   V   G   A   D   N   E 2790            2800            2810            2820            2830
GCA ACT AAT GCA GCA ACA TTC AAT GGA TAA GAA CAA TAA TTA AGC C
 A   T   N   A   A   T   F   N   G   X   E   Q   X   L   S
```

FIG. 1G

CNBr Peptide #1   (corresponds to nucleotides #1093-1122)
    M G T D N I I T Y H CNBr Peptide #2   (corresponds to nucleotides #1647-1674)
    N K E A D K E A Y Aminoterminal Sequence
    G K L N E F S A D I D Y Y D L

FIG. 2

```
      1280       1290       1300       1310       1320       1330
I  AAACATGTTCATTAATTGAAACTAGAGAAAAAGTCCAAGAAGTTGATTTGTGTGCAGAAG
   ::::::::::::::::::::::::::::::::::::::::::::::::::::::::::::
II AAACATGTTCATTAATTGAAACTAGAGAAAAAGTCCAAGAAGTTGATTTGTGTGCAGAAG
           160       150       140       130       120       110

1340       1350       1360       1370       1380       1390
I  AAACTAAGAATGGAGGAGTTCCATTCAAATGTAAGAATAACAATTGCATTATTGATCCTA
   ::::::::::::::::::::::::::::::::::::::::::::::::::::::::::::
II AGACTAAGAATGGAGGAGTTCCATTCAAATGTAAGAATAACAATTGCATTATTGATCCTA
           100        90        80        70        60        50

1400       1410       1420       1430       1440
:  ACTTTGATTGTCAACCTATTGAATGTAAGATTCAAGAGATTGTTATTA
   ::::::::::::::::::::::::::::::::::::::::::::::::
II ACTTTGATTGTCAACCTATTGAATGTAAGATTCAAGAGATTGTTATTA
            40         30        20        10
```

```
         160           150            140           130          120
    AAA CAT GTT CAT TAA TTG AAA CTA GAG AAA AAG TCC AAG AAG TTG ATT
     T   C   S   L   I   E   T   R   E   K   V   Q   E   V   D   L
           110           100            90            80
    TGT GTG CAG AAG AGA CTA AGA ATG GAG GAG TTC CAT TCA AAT GTA AGA
     C   A   E   E   T   K   N   G   G   V   P   F   K   C   K   N
     70            60             50            40           30
    ATA ACA ATT GCA TTA TTG ATC CTA ACT TTG ATT GTC AAC CTA TTG AAT
     N   N   C   I   I   D   P   N   F   D   C   Q   P   I   E   C
        20           10
    GTA AGA TTC AAG AGA TTG TTA TTA
     K   I   Q   E   I   V   I
```

```
         1280          1290           1300          1310         1320
    AAA CAT GTT CAT TAA TTG AAA CTA GAG AAA AAG TCC AAG AAG TTG ATT
     T   C   S   L   I   E   T   R   E   K   V   Q   E   V   D   L
          1330          1340           1350          1360         1370
    TGT GTG CAG AAG AAA CTA AGA ATG GAG GAG TTC CAT TCA AAT GTA AGA
     C   A   E   E   T   K   N   G   G   V   P   F   K   C   K   M
          1380          1390           1400          1410         1420
    ATA ACA ATT GCA TTA TTG ATC CTA ACT TTG ATT GTC AAC CTA TTG AAT
     N   N   C   I   I   D   P   N   F   D   C   Q   P   I   E   C
          1430          1440
    GTA AGA TTC AAG AGA TTG TTA TTA
     K   I   Q   E   I   V   I   T
```

FIG. 3

PURIFIED DNA OF THE 170-KD SURFACE GAL/GALNAC ADHERENCE LECTIN OF PATHOGENIC E. HISTOLYTICA

CROSS-REFERENCE TO RELATED APPLICATION

This application is a continuation-in-part of U.S. Ser. No. 479,691, filed Feb. 13, 1990 and of U.S. Ser. No. 456,579, filed Dec. 29, 1989, now U.S. Pat. No. 5,804,608 which is a continuation of U.S. Ser. No. 143,626, filed Jan. 13, 1988 now abandoned.

TECHNICAL FIELD

The invention relates to diagnostics and therapeutics for *Entamoeba histolytica* infection. More specifically, the invention is directed to diagnostic methods which take advantage of the genes encoding the Gal/GalNAc lectin of this amoeba, and specifically cDNA encoding the 170 kd heavy chain subunit.

BACKGROUND ART

*Entamoeba histolytica* infection is extremely common and affects an estimated 480 million individuals annually. However, only about 10% of these persons develop symptoms such as colitis or liver abscess. The low incidence of symptom occurrence is putatively due to the existence of both pathogenic and nonpathogenic forms of the amoeba. As of 1988, it had been established that the subjects who eventually exhibit symptoms harbor "zymodemes" which have been classified as such on the basis of their distinctive hexokinase and phosphoglucomutase isoenzymes. The pathogenic forms are not, however, conveniently distinguishable from the nonpathogenic counterparts using morphogenic criteria.

The distinction between pathogenic and nonpathogenic strains in diagnosis is of great practical importance, because only persons infected with *E. histolytica* who will develop the disease should be treated. This is bad enough in developed countries where it would at least be possible economically to treat every carrier with a known effective drug (metronidazole); it is, of course, undesirable to administer such drugs unnecessarily. In less developed countries, the cost of these unnecessary administrations is significant enough to have a dramatic negative impact on the resources for overall health care.

There is an almost perfect correlation between infection with a pathogenic zymodeme and development of symptoms and between infection with a nonpathogenic zymodeme and failure to develop these symptoms. As a general proposition, only pathogenic strains can be grown axenically (i.e., in the absence of an associated microorganism) and nonpathogenic strains have been made to grow in this manner only by "training" them to do so in a series of media alterations beginning with attenuated bacteria. The adaptation was accompanied by exhibition of the enzyme pattern characteristic of pathogenic strains (Mirelman, D., et al., *Infect Immun* (1986) 54:827-832). This work has not been repeatable in other laboratories, and more recent work on genomic differences (see below) indicates that the pathogenic and nonpathogenic forms are separate species.

It is known that *E. histolytica* infection is mediated at least in part by the "Gal/GalNAc" adherence lectin which was isolated from a pathogenic strain and purified 500 fold by Petri, W. A., et al., *J Biol Chem* (1989) 264:3007-3012. This successful isolation and purification was preceded by the production of mouse monoclonal antibodies which inhibit the in vitro adherence of the amoebic trophozoites; the antibodies were prepared from immortalized cells from spleens of mice immunized with sonicated trophozoites grown in axenic culture after having originally been isolated as a pathogenic strain from an affected subject. (Ravdin, J. I., et al., *Infect Immun* (1986) 53:1-5.) The cells were screened by the ability of the supernatants to inhibit adherence of the trophozoites to target tissue. All of these reported monoclonal antibodies, therefore, are presumably immunoreactive with the Gal/GalNAc surface adhesion of the pathogen. The Gal/GalNAc lectin was then prepared by galactose affinity chromatography and reported in 1987. (Petri, W. J., et al., *J Clin Invest* (1987) 80:1238-1244). Studies of serological cross-reactivity among patients having symptomology characteristic of *E. histolytica* pathogenic infection, including liver abscess and colitis, showed that the adherence lectin was recognized by all patients' sera tested (Petri, Jr., W. A., et al., *Am J Med Sci* (1989) 296:163-165).

The purified "Gal/GalNAc" lectin was shown to have a nonreduced molecular weight of 260 kd on SDS-PAGE. After reduction, with beta-mercaptoethanol, the lectin separated into two subunits of 170 and 35 kd MW. Further studies showed that antibodies directed to the 170 kd subunit were capable of blocking surface adhesion to test cells, and therefore, the 170 kd subunit is believed to be of primary importance in mediating adhesion.

Despite the generally interesting and useful results cited above, the ability to diagnose the presence or absence of pathogenic strains of *E. histolytica* has proved difficult. Since both pathogens and nonpathogens are morphologically similar, microscopic tests are not particularly useful. ELISA techniques have been used to detect the presence or absence of *E. histolytica* antigen in both stool specimens and in sera, but these tests do not seem to distinguish between the pathogenic and nonpathogenic strains. Root et al., *Arch Invest Med* (Mex) (1978) 9: Supplement 1:203, pioneered the use of ELISA techniques for the detection of amoebic antigen in stool specimens using rabbit polyclonal antiserum. Various forms of this procedure have been used since, some in correlation with microscopic studies, and all using polyclonal antisera. None of these, apparently, pinpoints the instances of infection with the pathogenic as opposed to nonpathogenic form. See, for example, Palacios et al., *Arch Invest Med* (Mex) (1978) 9: Supplement 1:203; Randall et al., *Trans Roy Soc Trop Med Hyg* (1984) 78:593; Grundy, *Trans Roy Soc Trop Med Hyg* (1982) 76:396; Ungar, *Am J Trop Med Hyg* (1985) 34:465.

These studies on stool specimens are summarized in *Amebiasis: Human Infections by Entamoeba Histolytica,* J. Ravdin, ed. (1988) Wiley Medical Publishing, pp. 646-648. Similar methods to detect characteristic *E. histolytica* antigens in serum and in liver abscess fluid are equally unable to distinguish pathogens from nonpathogens (ibid., pp. 661-663). As summarized in this article, as of 1988, the only known way to distinguish pathogenic from nonpathogenic forms of this amoeba was through characterizing the isoenzyme pattern using electrophoresis.

Recently it has been shown by two different groups that differences between pathogenic and nonpathogenic strains can be demonstrated using comparisons of DNA isolates. Garfinkel, L. I.. et al., *Infect Immun* (1989) 57:926-931 developed DNA probes which hybridize to DNA isolated from *E. histolytica* and four types of restriction fragment length patterns were obtained. These patterns correlated with pathogenic/nonpathogenic distinctions. Similarly, Tannich, E., et al., *Proc Natl Acad Sci* (1989) 86:5118-5122 probed cDNA libraries constructed from various strains and showed that pathogenic isolates were genetically distinct from nonpathogenic ones. However, these techniques require the culture of the organisms isolated from patients to obtain sufficient quantities for testing, and are thus time consuming and labor intensive.

Strachan, W. D., et al., *Lancet* (1988) 561-562, report the production of two monoclonal antibodies designated 22.3 and 22.5 which were members of a large group prepared by standard procedures from mice immunized with axenic cultures of a pathogenic *E. histolytica* strain NIH200/ATCC 30458. These monoclonal antibodies were tested in an immunofluorescence assay with cultures obtained from both putatively invasive and noninvasive strains, and appeared to immunoreact only with culture samples of invasive strains. There is no indication in this publication as to the manner of screening for antibodies with this characteristic, it is not known to what target these antibodies bond, nor would it be possible, without these specific antibodies, to reproduce this result. The test described requires intact *E. histolytica* and therefore cannot be applied in serum, urine or liver abscess fluid and can only be applied to stool samples which are freshly collected.

It would be highly desirable to have a relatively simple clinical test which would detect the presence of *E. histolytica* antigen in samples taken from patients and to be able to distinguish whether these antigens are associated with pathogenic or nonpathogenic strains. The present invention offers such a test, by employing conventional immunoassay procedures using monoclonal antibody reagents which are specifically immunoreactive with pathogenic and/or nonpathogenic Gal/GalNAc adherence lectin.

DISCLOSURE OF THE INVENTION

The invention provides diagnostic tests which permit the assessment of patients for invasive *E. histolytica* infection. The tests comprise the use of DNA hybridization with respect to cDNA encoding the 170 kd subunit of the adherence lectin. Pathogenic and nonpathogenic strains can be distinguished by use of this test. In addition, the availability of the cDNA encoding the subunit permits the interruption of the production of the adherence lectin by providing an antisense form of the cDNA.

Thus, in one aspect, the invention is directed to a method to detect the presence or absence of pathogenic or nonpathogenic *E. histolytica* in a biological sample, which method comprises subjecting the sample to polymerase chain reaction (PCR) using primers framing a region of the 170 kd heavy chain of the Gal/GalNAc adherence lectin which is characteristic of the pathogenic or nonpathogenic form as the case may be and probing the amplified DNA under stringent conditions with an oligomer corresponding to said characteristic portion. In another aspect, the invention is directed to a method of detecting the presence or absence of pathogenic or nonpathogenic *E. histolytica* which comprises subjecting the sample to PCR using primers corresponding to at least one region which is characteristic of either the pathogenic or nonpathogenic cDNA and probing the amplified DNA with an appropriate oligomer.

In still another aspect, the invention is directed to methods to interrupt the production of the 170 kd heavy chain of the adherence lectin by supplying to a subject or an *E. histolytica* culture the complement to the DNA encoding at least a portion of the 170 kd subunit of the adherence lectin. Other aspects include kits, vectors and pharmaceuticals directed to these purposes.

BRIEF DESCRIPTION OF THE DRAWINGS

FIG. 1 shows the nucleotide sequence and deduced amino acid sequence corresponding to the 170 kd heavy chain of the adherence lectin from NIH303.

FIG. 2 shows the peptide sequence of the CNBR derived fragment of NIH303.

FIG. 3 shows a comparison of the nucleotide sequence of a portion of the cDNA encoding the adherence lectin from a pathogenic and a nonpathogenic strain.

MODES FOR CARRYING OUT THE INVENTION

The present invention provides cDNA sequences which are useful in diagnostic assays for both pathogenic and nonpathogenic forms of *E. histolytica*. The diagnostic assays can be conducted on biological samples derived from cell cultures or from subjects at risk for infection. The assays utilize hybridization probes and by the design of the assay can distinguish pathogenic from nonpathogenic forms of the amoeba. In addition, the availability of the cDNA provides an opportunity for preventing the production of the adherence lectin using an "antisense" approach.

DEFINITIONS

As used herein, a nucleotide sequence "corresponding to" a referent nucleic acid refers to a sequence which is substantially the same as or complementary to the referent nucleic acid. Thus, a sequence "corresponding to" a region of the nucleic acid encoding the 170 kd subunit refers to a sequence which is the same as that region or complementary to it. It will be apparent from the context whether this sequence must be as found in the organism or may include degenerate sequences. Where hybridization, PCR amplification processes or antisense effects are the subject matter, degenerate sequences are not workable. For recombinant production of the protein, they are.

By "substantially" is meant homology is sufficient to provide the requisite hybridization to target under the conditions the DNA is employed. Similarly, by "effective fragment" is meant a fragment of sufficient size to provide the requisite hybridization to target under the conditions the DNA is employed.

A nucleotide sequence "characteristic of" a pathogenic or nonpathogenic strain refers to a nucleotide sequence which differentiates between these types of strains. Thus, a nucleotide sequence "characteristic of" a pathogenic *E. histolytica* refers to a nucleotide sequence wherein the analogous sequence in the nonpathogenic strain is not identical and is characteristically different from that of the sequence in the pathogenic strain.

A "composite" nucleotide sequence refers to a nucleotide sequence which in part corresponds to the sequence as it appears in a pathogenic strain, and in part as it appears in a nonpathogenic strain of *E. histolytica.*

An "analogous" region of a DNA refers to the sequence which encodes the referent protein or peptide sequence in a different *E. histolytica* strain.

"Replicon" refers to a DNA vector which is capable of self-replication when transformed into a suitable host, the context most frequently used herein when transformed into *E. histolytica.*

The diagnostic tests involve hybridization under various levels of hybridization stringency, and these levels are defined as follows:

low stringency corresponds to washing filters in 0.2×SSC, 0.1% SDS at 37° C. (1×SSC is 0.15M NaCl, 0.015M Na citrate, SDS- Na lauryl sulfate);

high stringency corresponds to washing in 0.2×SSC, 0.1% SDS at 65° C.;

moderate stringency corresponds to washing in 0.2×SSC, 0.1% SDS at 45° C.

As used herein, "immunospecific" with respect to a specified target means that the antibody thus described binds that target with significantly higher affinity than that with which it binds to alternate haptens. The degree of specificity required may vary with circumstances, but typically an antibody immunospecific for a designated target will bind to that target with an affinity which is at least one or two, or preferably several orders of magnitude greater than that with which it binds alternate haptens.

Furthermore, as used herein, the term "antibody" refers not only to immunoglobulins per se, but also to fragments of immunoglobulins which retain the immunospecificity of the complete molecule. Examples of such fragments are well known in the art, and include, for example, Fab, Fab', and F(ab')$_2$ fragments. The term "antibody" also includes not only native forms of immunoglobulins, but forms of the immunoglobulins which have been modified, as techniques become available in the art, to confer desired properties without altering the immunospecificity. For example, the formation of chimeric antibodies derived from two species is becoming more practical. In short, "antibodies" refers to any component of or derived form of an immunoglobulin which retains the immunospecificity of the immunoglobulin per se.

The term "pathogenic forms" of *E. histolytica* refers to those forms which are invasive and which result in symptomology in infected subjects. "Nonpathogenic forms" refer to those forms which may be harbored asymptomatically by carriers.

"Gal/GalNAc lectin" refers to a glycoprotein found on the surface of *E. histolytica* which mediates the adherence of the amoeba to target cells, and which mediation is inhibited by galactose or N-acetylgalactosamine. The Gal/GalNAc lectin refers specifically to the lectin reported and isolated by Petri et al. (supra) from the pathogenic strain HMI-IMSS, and to the corresponding lectin found in other species of *E. histolytica.* The "170 kd subunit" refers to the large subunit obtained by Petri et al. upon reduction of the Gal/GalNAc lectin and its corresponding counterparts in other species.

The "antibodies" described herein are immunospecific for the 170 kd subunit of the Gal/GalNAC lectin associated with *Entamoeba histolytica.* Three categories of monoclonal antibodies have been prepared. One category of antibody is immunospecific for epitopes which are found on the 170 kd subunit of Gal/GalNAc lectin which are "unique" to pathogenic forms. These antibodies are capable, therefore, of immunoreaction to a significant extent only with the pathogenic forms of the amoeba or to the 170 kd subunit of lectin isolated from pathogenic forms. Conversely, a second set of monoclonal antibodies is immunoreactive with epitopes which are "unique" to the 170 kd subunit of Gal/GalNAc lectin which is found in nonpathogenic forms. Thus, these antibodies are immunoreactive to a substantial degree only with the nonpathogenic amoeba or their lectins and not to the pathogenic forms. Finally, a third category of monoclonal antibodies is immunoreactive specifically with epitopes common to pathogenic and nonpathogenic forms and contained in the 170 kd subunit of the Gal/GalNAc lectin. These antibodies are capable of immunoreaction with the subunit or with the amoeba regardless of pathogenicity.

With respect to the monoclonal antibodies described herein, those immunoreactive with epitopes 1 and 2 of the 170 kd subunit isolated from the pathogenic strain exemplified are capable of reacting, also, with the corresponding epitopes on nonpathogens. On the other hand, those immunoreactive with epitopes 3-6 are capable of immunoreaction only with the 170 kd subunit of pathogenic strains. By applying the techniques for isolation of the pathogenic 170 kd subunit to amoeba which are nonpathogenic, a 170 kd subunit can be obtained for immunization protocols which permit the analogous preparation of Mabs immunoreactive with counterpart epitopes 3-6 in the nonpathogenic forms.

The monoclonal antibodies reported in the art, as set forth in the Background section above, were prepared using a screening procedure which screens for inhibition of an adherence of the amoeba to target cells. Therefore, the prior art antibodies are distinct from those which bind to epitopes 1, 2 and 3, which are shown hereinbelow either to enhance or to have no effect on the binding of the amoeba to target cells or proteins. Accordingly, those antibodies which immunoreact with epitopes 1, 2 and 3 are not available in the art.

The monoclonal antibodies of the invention are prepared by culturing immortalized cell lines which are capable of secreting them. The culturing of these lines is generally done in two ways—through in vitro culture methods with nutrients as generally understood, or by injection into suitable hosts, such as mice, in order to permit proliferation in vivo, with subsequent recovery of the mabs from ascites fluid. As used herein, "culturing" an immortalized cell line and "recovering the mabs from the culture" includes the procedures using both of these approaches.

Preparation of Purified Gal/GalNAc Lectin

The preparation of a highly purified form of the Gal/GalNAc lectin derived from a pathogen of *E. histolytica* is described in detail in Example 1. The preparation comprises an affinity chromatography step wherein monoclonal antibodies immunospecific to the 170 kd subunit of the reduced form of the Gal/GalNAc lectin are used as an affinity ligand to isolate the lectin from a solubilized preparation of the amoeba. The isolated lectin can be then reduced using standard methods, such as contact with a sulfhydryl reducing agent, for example dithiothreitol or beta-mercaptoethanol, to obtain the 170 kd subunit which is significant in mediating adhesion. Either the isolated 170 kd subunit or the purified lectin itself may be used for immunization to obtain antibody preparations, and in serological testing.

In a manner similar to that set forth in Example 1 as applied to purification of the Gal/GalNAc lectin from pathogenic strains, nonpathogenic lectin may also be purified to a similar level of purity by employing as affinity ligands in the affinity chromatography step monoclonal antibodies which are immunospecific for epitopes which are shared by both pathogenic and nonpathogenic forms. Two such monoclonal preparations are prepared as illustrations herein—those immunoreactive with epitope 1 and those immunoreactive with epitope 2. By use of these monoclonal antibody preparations as affinity ligands, the purified Gal/GalNAc lectin from either pathogenic or nonpathogenic forms may be prepared.

Preparation of Monoclonal Antibodies

The monoclonal antibodies described below are prepared by immunization protocols using the isolated and purified Gal/GalNAc lectins of the invention or the 170 kd subunits obtained by reduction thereof. Use of these lectins in purified and isolated form as immunogens, as well as their availability for use in screening the monoclonal preparations obtained greatly facilitates the preparation and identification of suitable monoclonal antibodies.

For immunization, standard protocols are employed, and any suitable vertebrate, typically a mammal, such as rats, mice, rabbits, and the like, can be used as the subject. When sufficient titers are obtained, the sera are harvested. The sera prepared as above are useful polyclonal compositions which, it has been found, are required for recovery of recombinant clones which express the genes encoding the 170 kd heavy subunit.

If monoclonals are desired, the antibody-producing cells of the subject, preferably spleen cells, are subjected to immortalization protocols, most conveniently those for the formation of hybridomas as set forth originally by Kohler and Millstein. However, additional techniques for immortalization such as viral infection may also be used.

The immortalized cells are then screened for the production of the desired mabs. Generally, the supernatants of the cultured immortalized cells are tested in standard immunoassays, such as ELISA or RIA, which employ as antigen the purified lectin or subunit used as an immunogen. Positively reacting supernatants are then further tested. It is convenient to verify immunoreactivity with the 170 kd subunit by using, as antigen in the assay or in Western blots, the reduced form of the isolated lectin.

The supernatants are then tested for cross-reactivity with the alternate forms of the lectin or subunit. For example, supernatants of antibody-secreting cells prepared from subjects immunized by pathogenic *E. histolytica* are tested by immunoassay against the purified lectin, or other lectin-containing antigen composition of nonpathogenic amoeba. Conversely, supernatants of antibody-secreting cells of subjects immunized with the lectin from nonpathogenic forms are checked for cross-reactivity with the lectin or other antigen-containing composition derived from the pathogenic alternatives.

Thus, monoclonal antibody preparations are obtained which are either immunoreactive with epitopes shared by both pathogens and nonpathogens, or with epitopes which are unique to the form from which they are derived.

Retrieval of cDNA

Expression libraries in λgt-11 were probed using the above-described monoclonal antibodies without success. Degenerate probes designed based on the amino terminal sequence of the purified pathogenic Gal/GalNAc lectin of Example 1 were also unsuccessful in retrieving the 170 kd subunit-encoding DNA. However, polyclonal antisera prepared from the purified Gal/GalNAc lectin as described above were immunoreactive with an *E. coli* transformed with a λgt-11 vector which contained a 2.0 kb cDNA insert. The sequence and deduced amino acid sequence of this insert are shown in FIG. 1.

Verification of the identity of the clone as bearing cDNA encoding the heavy subunit of the pathogenic strain NIH303 of *E. histolytica* was obtained by comparison of the deduced amino acid sequence with the cyanogen bromide cleavage sequence internal to the peptide. This sequence is shown in FIG. 2.

The availability of this cDNA permits the recovery of analogous cDNA from other strains of *E. histolytica*, both pathogenic and nonpathogenic using the standard methods described in Maniatis et al. and using the cDNA shown in FIG. 1 as a probe under stringent conditions. Thus, the retrieval of the cDNA shown in FIG. 1 makes available 170 kd subunit-encoding cDNA from all *E. histolytica* strains.

The Assay

For the conduct of the assay of the invention, samples are prepared and any amoebae contained therein solubilized according to standard procedures for the type of sample provided. Stool samples are treated as described, for example, by Ungar, et al., *Am J Trop Med Hyg* (1985) 34:465. Serum or plasma samples are diluted serially in phosphate buffered saline. Stool, serum or plasma samples are preferred, although other biological fluids or biopsy materials can also be used.

The DNA is extracted from the sample by the method of Kawasaki, E. S., in "PCR Protocols," Innis, M. A., et al., Eds., (1990) Academic Press, Ch. 18, p. 153 et seq. Briefly, in this protocol, the sample is lyophilized and resuspended in 100 $\mu$l of 50 Mm Tris, pH 8.3, 150 mM NaCl, 0.5% NP40. Proteinase K is added to 100 $\mu$g/ml. The sample is incubated at 55° C. for one hour, boiled for 3 minutes, and then placed on ice. After cooling, the sample is pelleted for 5 minutes in a microfuge and the supernatant is saved and either stored at 4° C. or used immediately. About 5 $\mu$l of the supernatant is used as a DNA template for further amplification per 50 $\mu$l reaction mixture in this procedure.

For preparation of standards, identified trophozoites are used in the initial preparation. Approximately $2 \times 10^6$ trophozoites are washed once with PBS, pelleted, lyophilized and stored at 200° C. for future use. About 10 mg of lyophilized amoebae are then used in the extraction.

The presence or absence of DNA associated with pathogenic or nonpathogenic strains can then be assessed using a protocol which takes advantage of nucleic acid sequence differences between these types of strains. All protocols involve amplification of the DNA using the polymerase chain reaction.

The PCR reaction is conducted using standard procedures, with primers designed to match specific regions of the target. In one approach, the primers are designed to frame a region of the DNA which is characteristic of the pathogenic or nonpathogenic form as desired. Thus, only a characteristic region will be amplified for detection with probe. The probe is then selected to correspond to that region specifically. Pathogenic strains are then distinguishable from nonpathogenic strains by their ability to hybridize to a probe corresponding to the region as it appears in the pathogenic strains; similarly, nonpathogens are detectable by their ability to hybridize with probes which correspond to sequences characteristic of nonpathogenic strains.

In an alternate approach, the choice of primer is used to distinguish between the pathogens and nonpathogens. In this approach, at least one of the primers used in the PCR reaction will correspond to the sequence which is characteristic of one or the other type of strain. Thus only the desired sequences will be amplified and detected by probe. In this instance, the probe used can be from either pathogenic or nonpathogenic strains or a composite thereof, and the stringency of the hybridization conditions can be adjusted to accommodate the selection of the probe; the stringency will be high, low or moderate depending on the degree of probe homology.

Where probes corresponding to the region to be detected are used, high stringency is generally employed. In the first method set forth above, high stringency is needed in order to distinguish between pathogenic and nonpathogenic strains; in the second approach which relies on characterization through selection of PCR primers, low stringency can be used since the distinction between pathogen/nonpathogen has already taken place. The hybridization to probe is detected using conventional techniques and under the stringency conditions set forth hereinabove.

Kits suitable for the above-described methods of diagnosis are also provided by the invention. These kits include, at a minimum, the appropriate primers, probes, additional reagents if desired, and instructions for conduct of the assay.

Antisense Methods

The DNAs of the invention can also be used to control the production of the 170 kd Gal/GalNAc binding lectin subunit using antisense technology. The complement to the DNA of FIG. 1, or a significant portion thereof, is supplied to an amoeba culture or to host organism harboring *E. histolytica* infection using standard methods of administration, such as those set forth in *Remington's Pharmaceutical Sciences*, Mack Publishing Company, Easton, Pa., latest edition. Preferably, for in vivo treatment of a subject, the complement is provided by injection, and formulated using conventional excipients therefor, such as Ringer's solution, Hank's solution, and the like. Oral administration with proper formulation can also be effected. While most administration is systemic, in the case of localized conditions such as solid tumor growth, administration may be topical or otherwise local. Slow release mechanisms for drug delivery may also be used.

Alternatively, the complementary nucleotide sequence may be generated in situ by providing an expression system which contains the cDNA of FIG. 1 or its analogous DNA from other *E. histolytica* strains or an effective fragment thereof in a "reverse orientation" expression system. The expression system may either be designed to be operable in the host subject, such as a mammalian subject wherein the reverse oriented *E. histolytica* encoding sequence is under the control of, for example, an SV-40 promoter, an adenovirus promoter, and the like so that the complement is transcribed in situ. When used in a cell culture of *E. histolytica*, the expression system will be provided on a replicon compatible with the *E. histolytica* strain.

The following examples are intended to illustrate but not to limit the invention:

EXAMPLE 1

Preparation of Antibodies Immunoreactive with the 170 kd Subunit

Axenic *E. histolytica*, pathogenic strain HMI-IMSS were grown in medium TYIS-33 (trypticase yeast extract, iron and serum) with 100 U/ml penicillin and 100 mg/ml streptomycin sulfate at 37° C. in 250 ml plastic tissue culture flasks. The amoebae were harvested after 72 hours of growth by centrifugation at 150×g for 5 min at 4° C. and washed twice in ice cold 75 mM Tris, 65 mM NaCl, pH 7.2.

The trophozoites harvested from four 250 ml flasks were preincubated on ice in 5 ml of 75 mM Tris, 65 mM NaCl with a 1:1000 dilution of diisopropylfluorophosphate before solubilization in 10 ml of 150 Mm NaCl, 50 mM Tris, pH 8.3, 0.5% Nonidet P-40, 5 mM EDTA and 2 mM phenylmethylsulfonyl fluoride. The solubilized amoebae were microfuged for 10 min and the supernatant was applied at 4° C. to a monoclonal antibody affinity column consisting of 2 mg each of protein A-purified anti-lectin monoclonal antibodies H85, 7F4, 5B8, 3F4 and 6D2 immobilized on 1-2 ml of Affi-Gel 10. This purification method and these antibodies are described in Petri, Jr., W. A., et al., *J Biol Chem* (1989) 264:3007-3012 (supra), incorporated herein by reference. The supernatant was recirculated through the column with a peristaltic pump overnight, and the column was then washed with 15 ml of solubilization buffer followed with 15 ml of phosphate-buffered saline, pH 7.5.

The bound lectin was eluted with 10 ml of 0.2N acetic acid, pH 2.5; immediately neutralized by collecting eluted fractions into a 50 ml tube containing 5 ml of 1.5M Tris, pH 8.8; dialyzed overnight against distilled water, frozen and lyophilized.

The purified lectin was used for immunization. Polyclonal antisera were obtained for use in the procedure of Example 4.

EXAMPLE 2

Preparation of Mabs

Immunized mice spleen cells from Example 1 were used for fusions to produce hybridomas as previously described in detail in Petri, Jr., W. A., et al., *J Clin Invest* (1987) 80:1238; Petri, Jr., W. A., et al., *J Biol Chem* (1989) 264:3007; and Ravdin, J. I., et al., *Infect Immun* (1986) 53:1, all cited above and all incorporated herein by reference.

Monoclonal antibodies were obtained from two fusions using spleen cells from BALB/C mice injected with purified lectin in complete and then in incomplete Freund's adjuvant followed by a final boost intrasplenically. The supernatants were assayed by standard ELISA using the lectin-coated (1 mg/well) microtiter plates and 36 positively-testing supernatants were obtained. The positive supernatants were then tested for immunoreactivity with the 170 kd lectin subunit by Western blot and 10 of the 36 were positive in this assay.

None of these Mabs were able to identify clones containing the 170 kd subunit-encoding DNA.

EXAMPLE 3

Determination of Sequence

The lectin 170 kd subunit purified to homogeneity in Example 1 was subjected to N-terminal sequencing and fragmented using CNBR to obtain internal sequence information. The results of these sequence determinations appear in FIG. 2. Probes designed on the basis of these sequences were unable to identify clones containing the 170 kd subunit-encoding DNA; however, matching of the DNA obtained as set forth in Example 4 with the sequence of the internal CNBR fragment sequence permitted verification that the correct cDNA had been obtained.

EXAMPLE 4

Cloning of cDNA from NIH303

Total RNA was isolated from pathogenic *E. histolytica* trophozoites, strain NIH303, by the method of Chirgwin et al., *Biochemistry* (1979) 18:5294–5299. PolyA+ RNA was isolated by PolyU Sepharose guanidinium isothiocyanate preparation as described by Edman et al., *Proc Natl Acad Sci USA* (1987) 84:3024–3028, and the cDNA was synthesized using the commercially available kit marketed by Amersham, Arlington Heights, Ill., according to the manufacturer's protocol. EcoRI linkers were added to the double-stranded cDNA and ligated and packaged in vitro into λgt11 according to the procedure of Maniatis et al., "Molecular Cloning: A Laboratory Cloning Manual" (1982) Cold Spring Harbor Laboratories, Cold Spring Harbor, N.Y., and as described by Davis and Young, *Proc Natl Acad Sci USA* (1983) 80:1194–1198.

Approximately 100,000 plaques were obtained using *E. coli* strain Y1090 which permits expression of fusion proteins from the recombinant bacteriophage. Plaques were plated and incubated at 42° C. until plaques were just barely visible (3–4 hours). A nitrocellulose filter that had been soaked in 10 mmol isopropyl β-D-thiogalactopyranoside was placed on top of the plates and the plates were incubated for 3.5 hours. The filters were removed and blocked with 3% BSA and incubated at room temperature with 1:100 dilution of rabbit anti-lectin antisera, prepared as set forth in Example 1, that had been preabsorbed with *E. coli* proteins. The filters were washed and incubated with alkaline phosphatase conjugated anti-Rabbit IgG.

After several hours at room temperature, the filters were washed and developed with alkaline phosphate substrate. Positive plaques were isolated and the procedure was repeated until a pure plaque was obtained. Reagents used were from a Protoblot kit from Promega (Madison, Wis.).

The purified positive plaque obtained was sequenced using standard techniques and the results showed the sequence set forth in FIG. 1. FIG. 1 provides the nucleotide sequence and deduced amino acid sequence corresponding to the 170 kd heavy chain of the adherence lectin.

EXAMPLE 5

Cloning of cDNA from Additional *E. histolytica* Strains

A cDNA library in *E. coli* is prepared from either a pathogenic or nonpathogenic strain of *E. histolytica* using the methods set forth in Example 4 above. The library is then probed with the cDNA of FIG. 1 or a 17 nucleotide or greater fragment thereof under stringent conditions. Analogous cDNA from the other known *E. histolytica* strains is thus recovered.

The cDNA encoding the 170 kd heavy subunit of the adherence lectin from a nonpathogenic strain was recovered and partially sequenced. A comparison of this partial sequence with the corresponding sequence in the pathogenic strain cDNA obtained in Example 4 is shown in FIG. 3. As indicated, there is extensive homology in this region.

We claim:

1. A DNA in purified and isolated form which consists essentially of a DNA encoding the 170 kd heavy chain of pathogenic *E. histolytica* Gal/GalNAc adherence lectin.

* * * * *